United States Patent
Sano et al.

(10) Patent No.: US 9,375,155 B2
(45) Date of Patent: Jun. 28, 2016

(54) DIAPHRAGM PUMP AND BLOOD PRESSURE MONITOR

(75) Inventors: Yoshihiko Sano, Kyoto (JP); Tomohiro Kukita, Amsterdam (NL)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 996 days.

(21) Appl. No.: 13/192,109

(22) Filed: Jul. 27, 2011

(65) Prior Publication Data

US 2011/0282223 A1 Nov. 17, 2011

Related U.S. Application Data

(63) Continuation of application No. PCT/JP2009/071119, filed on Dec. 18, 2009.

(30) Foreign Application Priority Data

Jan. 28, 2009 (JP) ................. 2009-016459

(51) Int. Cl.
*A61B 5/22* (2006.01)
*F04B 43/06* (2006.01)
(Continued)

(52) U.S. Cl.
CPC .............. *A61B 5/0235* (2013.01); *A61B 5/0225* (2013.01); *A61B 5/02141* (2013.01); *A61B 5/02233* (2013.01); *F04B 43/026* (2013.01); *F04B 1/148* (2013.01); *F04B 43/02* (2013.01)

(58) Field of Classification Search
CPC .............. A61B 5/02141; A61B 5/0235; A61B 5/0225; A61B 5/02233; F04B 1/148; F04B 43/02; F04B 43/026
USPC ................. 417/395, 413.1, 566, 533
See application file for complete search history.

(56) References Cited

U.S. PATENT DOCUMENTS

| 4,801,249 A * | 1/1989 | Kakizawa ............ A61B 5/0235 417/269 |
| 6,506,033 B2 * | 1/2003 | Fukami .................. F04B 1/148 417/420 |

(Continued)

FOREIGN PATENT DOCUMENTS

| CN | 2684161 Y | 3/2005 |
| JP | 07-210167 A | 8/1995 |

(Continued)

OTHER PUBLICATIONS

English Machine Translation of JP2005-030341.*
(Continued)

*Primary Examiner* — Peter J Bertheaud
*Assistant Examiner* — Dominick L Plakkoottam
(74) *Attorney, Agent, or Firm* — Osha Liang LLP (57) ABSTRACT

A diaphragm pump for achieving reduced pressure ripple of an exhausted gas is provided. The diaphragm pump is a pump for transporting a gas in accordance with change in volume of a pump chamber, and the diaphragm pump includes an exhaust valve permitting flow of the gas that flows out of the pump chamber and prohibiting a flow thereof in a reverse direction, an air chamber in which the gas that has flowed out of the pump chamber through the exhaust valve flows, an exhaust port through which the gas is exhausted to the outside of the diaphragm pump, and a through hole portion for restricting a flow rate of the gas that flows from the air chamber to the exhaust port.

4 Claims, 5 Drawing Sheets

(51) Int. Cl.
  *A61B 5/0235* (2006.01)
  *F04B 43/02* (2006.01)
  *A61B 5/021* (2006.01)
  *A61B 5/022* (2006.01)
  *A61B 5/0225* (2006.01)
  *F04B 1/14* (2006.01)

(56) References Cited

U.S. PATENT DOCUMENTS

| | | | | |
|---|---|---|---|---|
| 6,764,287 B2 * | 7/2004 | Yamakawa | .......... | F04B 43/0045 417/413.1 |
| 6,843,643 B2 * | 1/2005 | Fukami | ................ | F04B 43/026 137/855 |
| 2005/0169780 A1 * | 8/2005 | Fukami | ................ | F04B 43/026 417/413.1 |
| 2011/0028853 A1 * | 2/2011 | Sano | ................. | A61B 5/02141 600/490 |

FOREIGN PATENT DOCUMENTS

| | | |
|---|---|---|
| JP | 11-276447 A | 10/1999 |
| JP | 2003-139258 A | 5/2003 |
| JP | 2003-162283 A | 6/2003 |
| JP | 2004-263597 A | 9/2004 |
| JP | 2005-030341 A | 2/2005 |
| JP | 2005030341 A * | 2/2005 |
| JP | 4197441 B2 | 12/2008 |

OTHER PUBLICATIONS

Patent Abstracts of Japan, Publication No. 2003-162283, Publication Date: Jun. 6, 2003, 1 page.
Patent Abstracts of Japan, Publication No. 07-210167, Publication Date: Aug. 11, 1995, 1 page.
Patent Abstracts of Japan, Publication No. 2003-139258, Publication Date: May 14, 2003, 1 page.
Patent Abstracts of Japan, Publication No. 11-276447, Publication Date: Oct. 12, 1999, 1 page.
Patent Abstracts of Japan, Publication No. 2005-030341, Publication Date: Feb. 3, 2005, 1 page.
International Search Report issued in PCT/JP2009/071119 mailed on Feb. 9, 2010 and English translation thereof, 2 pages.
Office Action issued in Chinese Application No. 200980155505.2, mailed on Jun. 4, 2013, and translation thereof (12 pages).

* cited by examiner

DIAPHRAGM PUMP AND BLOOD PRESSURE MONITOR

This is a continuation of application Serial No. PCT/JP2009/071119 filed Dec. 18, 2009, the contents of which are incorporated herein by reference.

BACKGROUND OF THE INVENTION

1. Field of the Invention

The present invention relates to a diaphragm pump and a blood pressure monitor.

2. Description of the Background Art

In recent years, importance has increasingly been placed on self-management of a blood pressure and blood pressure monitors for home use have widely been available. In measuring a blood pressure, an arm band containing a bladder is wound around a part of a living body and air is sent into the bladder for pressurization. A blood pressure is measured based on artery information obtained by pressing the living body. For pressurization of the bladder, an air pump is used. The air pump includes a rubber-like diaphragm portion forming a pump chamber within a case, a piston provided in the diaphragm portion, and a drive element attached to the piston. As the drive element swings to cause the piston to carry out reciprocating motion, a volume of the pump chamber is varied. As a result of change in volume of the pump chamber, a pumping action for transferring the air is performed. The air pump is provided with a check valve, in order to avoid back flow of exhausted air and intake air.

Air is continuously exhausted from a tip end of the pump, in accordance with change in volume of the pump chamber. As the piston moves downward, air flows into the pump chamber, and as the piston moves upward, air is exhausted from the pump chamber. As the piston repeats up-down movement, pressure fluctuation of a gas discharged from the pump (hereinafter referred to as pressure ripple) is generated. As the pressure ripple of the pump is generated, its amplitude makes heaving sound (pressurization sound) larger and pump noise increases.

The pump included in the blood pressure monitor is connected to an air valve, a pressure sensor, and an arm band through an air tube. A pressure pulse wave of a human body detected at the arm band is measured by the pressure sensor. Here, in order to conduct accurate blood pressure measurement, pressure ripple generated from the pump should be eliminated to measure a pure pressure pulse wave of the human body. Therefore, various techniques for eliminating pressure ripple have conventionally been proposed (see, for example, Japanese Patent Laying-Open No. 2003-162283 (Patent Document 1), Japanese Patent Laying-Open No. 7-210167 (Patent Document 2), and Japanese Patent Laying-Open No. 11-276447 (Patent Document 3)).

Japanese Patent Laying-Open No. 2003-162283 (Patent Document 1) proposes an acoustic filter including a tank and a thin pipe, in which the tank and the thin pipe are formed by layering filter cases. Japanese Patent Laying-Open No. 7-210167 (Patent Document 2) proposes an acoustic filter including a tank and a thin pipe, in which the tank and the thin pipe are formed by layering a filter case and packing.

Japanese Patent Laying-Open No. 11-276447 (Patent Document 3) proposes a blood pressure monitor including a low-cut filter for outputting a ripple component of an air pump, a ripple suppression comparator receiving an output from the low-cut filter as an input, and an adder for adding the output from the ripple suppression comparator to an output from a volume compensation comparator. In addition, a method for eliminating a pump ripple signal in a blood pressure monitor, by causing a signal indicating a pressure within a cuff obtained by the pressure sensor to pass through the low-cut filter so as to obtain only the ripple component of the pump without including a blood pressure signal component, comparing a signal from the low-cut filter with a reference value of zero by using the ripple suppression comparator, adding an error signal output from the ripple suppression comparator to an error signal from the volume compensation comparator, inputting the resultant signal to a valve controller, and controlling a leakage valve, has been proposed.

Conventional methods proposed in Japanese Patent Laying-Open No. 2003-162283 (Patent Document 1), Japanese Patent Laying-Open No. 7-210167 (Patent Document 2), and Japanese Patent Laying-Open No. 11-276447 (Patent Document 3), however, are not methods for reducing the pressure ripple itself generated from the pump. Therefore, such a problem that pressurization noise due to the pressure ripple of the pump is large still remains. In addition, as the acoustic filter is provided at a pressure sensor inlet portion, such problems as complicated air pipe arrangement, increase in the number of parts, and cost increase arise. Moreover, the method described in Japanese Patent Laying-Open No. 11-276447 (Patent Document 3) requires the ripple suppression comparator, the low-cut filter, the valve controller, and the like, and the number of air system parts increases, which results in complicatedness.

SUMMARY OF THE INVENTION

The present invention was made in view of the above-described problems, and a primary object of the present invention is to provide a diaphragm pump capable of achieving reduced pressure ripple of a gas exhausted from the pump. In addition, another object of the present invention is to provide a blood pressure monitor including the diaphragm pump above.

A diaphragm pump according to the present invention is a pump for transporting a gas in accordance with change in volume of a pump chamber, and the diaphragm pump includes an exhaust valve for permitting flow of a gas that flows out of the pump chamber and prohibiting flow thereof in a reverse direction, an air chamber in which the gas that has flowed out of the pump chamber through the exhaust valve flows, an exhaust port through which the gas is exhausted via an exhaust path to outside of the diaphragm pump, and a partition wall portion for partition between the air chamber and the exhaust path. In the partition wall portion, a through hole portion for communication between the air chamber and the exhaust path is formed. The through hole portion restricts a flow rate of the gas that flows from the air chamber to the exhaust port.

In the diaphragm pump above, a plurality of pump chambers may be provided, and the air chambers and the through hole portions as many as the pump chambers may be provided.

In the diaphragm pump above, a plurality of pump chambers may be provided, a single air chamber may be provided, and the gases that have flowed out of the plurality of the pump chambers may gather in the air chamber.

A blood pressure monitor according to the present invention includes a cuff attached to a blood pressure measurement site of a subject and having a bladder filled with a gas. In addition, the blood pressure monitor includes the diaphragm pump according to any aspect above, for transferring the gas to the bladder. Moreover, the blood pressure monitor includes a pressure detection unit for detecting a pressure within the cuff. Further, the blood pressure monitor includes a measurement unit for measuring a blood pressure of the subject based on a pressure value detected by the pressure detection unit.

According to this diaphragm pump, the air chamber and the regulation portion are provided between the exhaust valve for letting the gas flow out of the pump chamber and the exhaust port through which the gas is exhausted to the outside of the diaphragm pump, to thereby form an acoustic filter. As a result of a function of this acoustic filter, pressure ripple of the gas exhausted from the pump can be reduced. Therefore, the acoustic filter at the pressure sensor inlet portion that has conventionally been used is no longer necessary and the pump can be reduced in size. In addition, as the pressure ripple can be reduced in the pump, pump noise due to the pressure ripple can be lowered.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention will be described hereinafter with reference to the drawings. In the drawings below, the same or corresponding elements have the same reference characters allotted, and description thereof will not be repeated.

In the embodiment described hereinafter, each component is not necessarily indispensable in the present invention unless otherwise specified. In addition, in the embodiment below, reference to the number, an amount or the like is merely by way of example unless otherwise specified, and the scope of the present invention is not necessarily limited to that number, that amount or the like.

Figure 1:
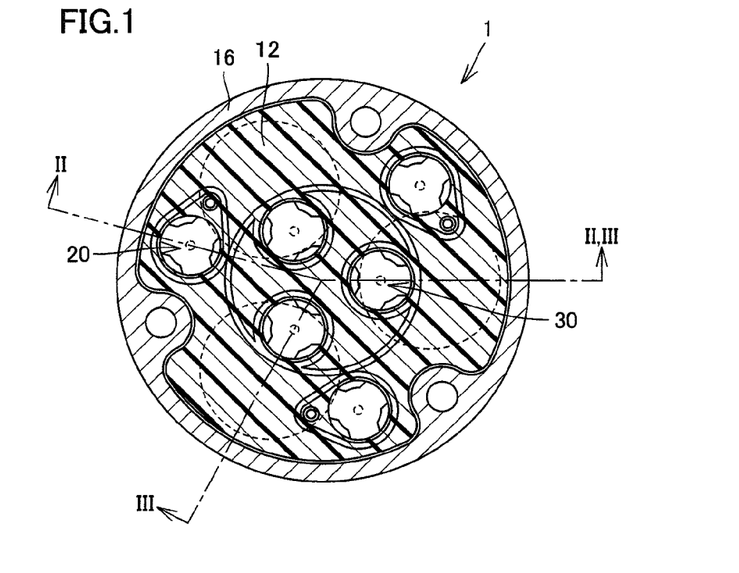
FIG. 1 is a schematic plan view showing a structure of a diaphragm pump according to the present invention.
Figure 2:
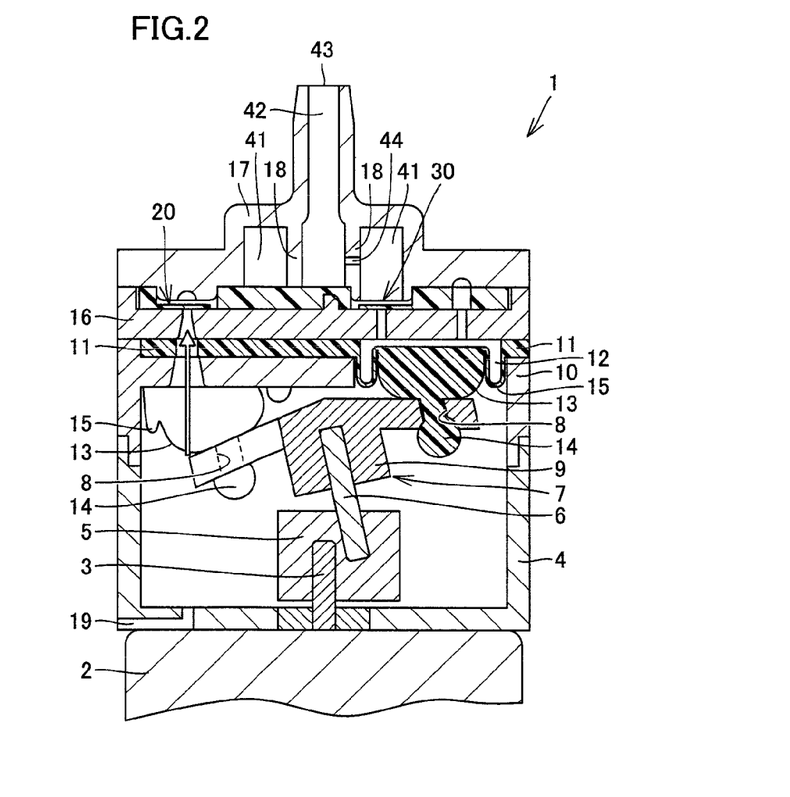
FIG. 2 is a schematic cross-sectional view of the diaphragm pump along the line II-II shown in FIG. 1.
Figure 3:
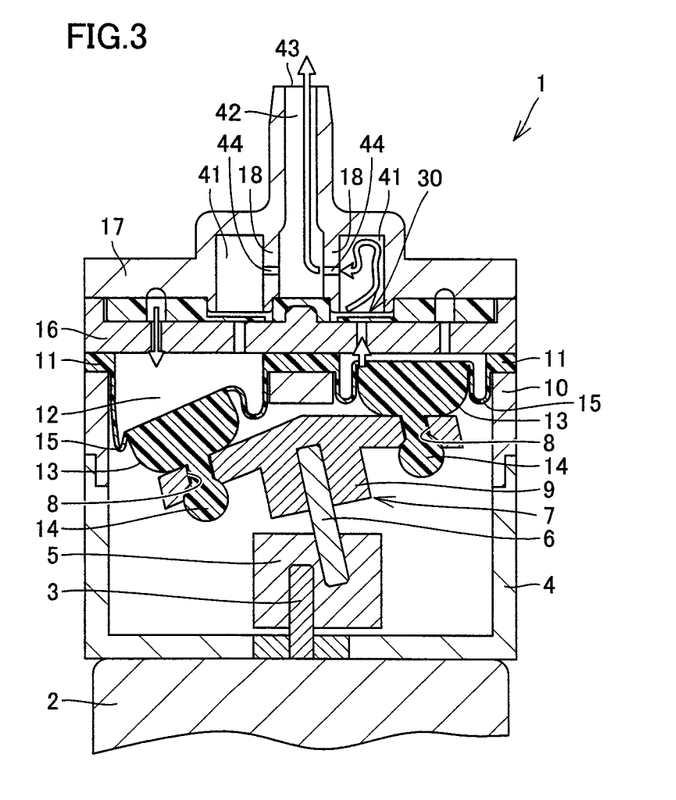
FIG. 3 is a schematic cross-sectional view of the diaphragm pump along the line shown in FIG. 1.

As shown in FIGS. 1 to 3, in a lower portion of a diaphragm pump 1, a motor 2 which is a small-sized DC motor is provided. An output shaft 3 rotating together with rotational movement of motor 2 is attached to motor 2. Output shaft 3 extends into a lower case 4 of diaphragm pump 1.

A rotation element 5 is fixed to an end portion of output shaft 3. Rotation element 5 carries out rotational movement integrally with output shaft 3. A drive shaft 6 is fixed to rotation element 5. A base end of drive shaft 6, which is one end portion fixed to rotation element 5, is located at a distance from an extension of the rotation center of output shaft 3. On the other hand, on the other end portion side of drive shaft 6, an extension of the central axis thereof intersects with the extension of the rotation center of output shaft 3. Drive shaft 6 is thus inclined with respect to output shaft 3.

A drive element 7 is rotatably inserted in the tip end side of drive shaft 6. Drive element 7 is formed to have an annular shape when viewed two-dimensionally. Drive element 7 includes three through holes 8 formed at intervals of 120°. A cylindrical support portion 9 extending in a direction in which drive shaft 6 extends is formed below drive element 7, and the tip end portion of drive shaft 6 is rotatably inserted in a hole provided in the center of support portion 9. An upper case 10 is arranged to surround drive element 7. Upper case 10 is fixed at its lower end portion to an upper end portion of lower case 4, by means of a screw function or the like.

A diaphragm main body 11 is provided on upper case 10. Diaphragm main body 11 is formed from an elastic material or the like such as soft and thin rubber and formed in a disc shape. Pump chambers 12 formed at regular intervals of an angle of 120° are formed under diaphragm main body 11. As shown in FIG. 1, pump chamber 12 is formed in an annular shape when viewed two-dimensionally.

A bell-shaped drive portion 13 is provided under pump chamber 12. A head portion 14 is formed at a tip end of drive portion 13, with a thin neck portion being interposed. Head portion 14 passes through a through hole 8 formed in drive element 7 and the neck portion is arranged to locate within through hole 8, so that diaphragm main body 11 and drive element 7 are assembled. To an outer circumference of drive portion 13, an extensible, thin-film-shaped diaphragm portion 15 is attached. Diaphragm portion 15 hermetically couples diaphragm main body 11 forming a peripheral portion of pump chamber 12 in an annular shape when viewed two-dimensionally and the outer circumference of drive portion 13 to each other.

A valve housing 16 covering pump chamber 12 from above as a lid is provided on diaphragm main body 11. Pump chamber 12 is formed such that it is surrounded by drive portion 13, diaphragm portion 15, diaphragm main body 11, and valve housing 16. It is noted that pump chamber 12 may be formed such that an inner surface of pump chamber 12 includes an inner surface of upper case 10.

A gas gathering body 17 is further provided on valve housing 16. An intake valve 20 and an exhaust valve 30 are arranged such that they lie between valve housing 16 and gas gathering body 17. Intake valve 20 is a check valve provided within an air passage for allowing flow of a gas into pump chamber 12. Exhaust valve 30 is a check valve provided within an air passage for allowing flow of a gas out of pump chamber 12. In the schematic plan view shown in FIG. 1, a plan view of diaphragm pump 1 in the cross-section where intake valve 20 and exhaust valve 30 are provided is shown.

A gas transported by diaphragm pump 1 is exhausted through an exhaust port 43 to the outside of diaphragm pump 1 via an air chamber 41 and an exhaust path 42 formed in gas gathering body 17. A part of gas gathering body 17 projects inward, to form a partition wall portion 18 for partition between air chamber 41 and exhaust path 42. A through hole portion 44 having a small diameter is formed in a part of partition wall portion 18, and air chamber 41 and exhaust path 42 communicate with each other through hole portion 44. A diameter of an air passage from air chamber 41 to exhaust port 43 is relatively small at through hole portion 44.

As shown in FIG. 1, pump chambers 12 are provided at three locations at intervals of an angle of 120°. Air that has flowed out of pump chamber 12 flows into air chamber 41 through exhaust valve 30. Three air chambers 41 are also provided and three through hole portions 44 each serving as an exit of air from air chamber 41 are also formed, in correspondence with three pump chambers, respectively. Namely, air chambers 41 and through hole portions 44 as many as pump chambers 12 are provided.

A space surrounded by lower case 4, upper case 10 and diaphragm main body 11 forms an internal space of diaphragm pump 1. An intake path 19 is formed at one location or a plurality of locations in at least any one of lower case 4 and upper case 10, so that the internal space of diaphragm pump 1 and the outside of diaphragm pump 1 communicate with each other. Atmospheric gas flows through intake path 19 into the internal space of diaphragm pump 1 from the outside.

Diaphragm main body 11 and drive portion 13 are hermetically coupled to each other by thin-film-shaped diaphragm portion 15. Therefore, the respective internal spaces of diaphragm pump 1 and pump chamber 12 are formed as spaces different from each other. The respective internal spaces of diaphragm pump 1 and pump chamber 12 are formed to have such a structure that they communicate with each other through an air passage including intake valve 20 only when intake valve 20 is open.

An operation of diaphragm pump 1 will be described hereinafter. When electric power is fed to motor 2 and output shaft 3 rotates, rotation of output shaft 3 is transmitted to drive shaft 6 through rotation element 5, and drive shaft 6 which is an inclined, eccentric rotation shaft rotates. Drive shaft 6 is rotatably assembled to drive element 7 and drive portion 13 in each pump chamber 12 is fixed to drive element 7 at the neck portion for coupling head portion 14. Therefore, as drive shaft 6 rotates, a portion where drive element 7 and each pump chamber 12 are assembled vibrates in an up-down direction with a phase difference of 120°.

This vibration causes drive portion 13 to carry out reciprocating motion in the up-down direction. Vibration of drive portion 13 in the up-down direction brings about extension and contraction of diaphragm portion 15, which results in periodic change in volume of pump chamber 12. Namely, when drive portion 13 moves downward, the volume of pump chamber 12 increases. When drive portion 13 moves upward, the volume of pump chamber 12 decreases. Pump chamber 12 is a variable-volume chamber formed such that its volume can be varied. As diaphragm portion 15 is formed from a thin, elastic material such as rubber and it can readily deform, diaphragm portion 15 can achieve a pumping action for transporting a gas based on the reciprocating motion of drive portion 13 supported by drive element 7 in a manner allowing reciprocating motion.

When drive portion 13 moves downward and the volume of pump chamber 12 increases, pump chamber 12 is reduced in pressure. When pump chamber 12 is reduced in pressure, a valve element of exhaust valve 30 comes in intimate contact with valve housing 16 and exhaust valve 30 is closed, so that back flow of air from air chamber 41 through exhaust valve 30 into pump chamber 12 is prevented. On the other hand, a valve element of intake valve 20 elastically deforms in accordance with change in pressure in pump chamber 12. Intake valve 20 thus opens, and air flows from the internal space of diaphragm pump 1 through intake valve 20 into pump chamber 12, as shown with a hollow arrow on the left in FIGS. 2 and 3.

When drive portion 13 moves upward and the volume of pump chamber 12 decreases, pump chamber 12 is raised in pressure. When pump chamber 12 is raised in pressure, the valve element of intake valve 20 comes in intimate contact with valve housing 16 and intake valve 20 is closed, so that back flow of air from pump chamber 12 into the internal space of diaphragm pump 1 is prevented. On the other hand, the valve element of exhaust valve 30 elastically deforms in accordance with change in pressure in pump chamber 12. Exhaust valve 30 thus opens, and air flows out of pump chamber 12 into air chamber 41 through exhaust valve 30, as shown with a hollow arrow on the right in FIG. 3.

As described above, by changing the volume of pump chamber 12 through reciprocating motion of drive portion 13 provided in each pump chamber 12, air is taken into pump chamber 12 through intake valve 20 or air is discharged from pump chamber 12 through exhaust valve 30, so that diaphragm pump 1 can transport air. Intake valve 20 functions as a check valve permitting flow of a gas from the internal space of diaphragm pump 1 to pump chamber 12 and prohibiting flow thereof in a reverse direction. Exhaust valve 30 functions as a check valve permitting flow of a gas that flows out of pump chamber 12 to exhaust port 43 and prohibiting flow thereof in a reverse direction.

The air that has flowed out of pump chamber 12 through exhaust valve 30 flows from exhaust port 43 to the outside through air chamber 41 and exhaust path 42 formed within gas gathering body 17, as described previously. Partition wall portion 18 provides partition between air chamber 41 and exhaust path 42. Air flows from air chamber 41 to exhaust path 42 through hole portion 44 formed in partition wall portion 18. Through hole portion 44 is formed such that a cross-sectional area of an air flow path is small relative to air chamber 41 and exhaust path 42, and flow of the air is regulated by through hole portion 44. Through hole portion 44 formed in partition wall portion 18 functions as a regulation portion for restricting a flow rate of air that flows from air chamber 41 through exhaust path 42 to exhaust port 43.

As air is intermittently discharged from pump chamber 12 in accordance with change in volume of pump chamber 12, air intermittently flows from pump chamber 12 into air chamber 41. Namely, the flow rate of air that flows out of pump chamber 12 is not always constant but it fluctuates. By employing a three-cylinder type diaphragm pump provided with three pump chambers 12 at regular intervals of an angle of 120°, fluctuation of a flow rate of air can be suppressed as compared with a single-cylinder type diaphragm pump having only a single pump chamber 12, however, fluctuation of a flow rate of air still remains. When a flow rate of air that flows out of the pump fluctuates, pressure ripple of the pump is generated and pump noise becomes greater.

In diaphragm pump 1 in the present embodiment, air that has flowed out of pump chamber 12 is temporarily stored in air chamber 41, and diaphragm pump 1 is adjusted such that a flow rate of air flowing from air chamber 41 to exhaust path 42 is regulated by through hole portion 44 and an amount of air that flows to exhaust path 42 can be more uniform. Diaphragm pump 1 in the present embodiment provided with air chamber 41 and through hole portion 44 achieves improved uniformity in a flow rate of air that flows from air chamber 41 to exhaust path 42.

Namely, diaphragm pump 1 includes air chamber 41 having a function of an accumulator for temporarily accumulating air that flows from pump chamber 12 to exhaust port 43, and through hole portion 44 for regulating a flow rate of air that flows out of air chamber 41 is formed in partition wall portion 18. Therefore, fluctuation of a flow rate of air that flows out of diaphragm pump 1 is suppressed. Thus, pressure fluctuation of air discharged from diaphragm pump 1, that is, pressure ripple, is suppressed. Air chamber 41 and through hole portion 44 function as an acoustic filter for eliminating pressure ripple of diaphragm pump 1.

The acoustic filter is thus arranged in an air passage from pump chamber 12 to exhaust port 43 and the acoustic filter is provided in diaphragm pump 1, so that pressure ripple can be reduced in diaphragm pump 1. As the pressure ripple is suppressed, pressurization sound is also lowered. Therefore, noise generated by diaphragm pump 1 can also be suppressed.

Figure 4:
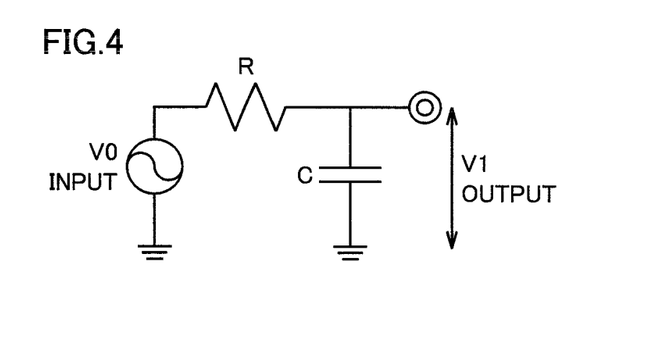
FIG. 4 is a circuit diagram illustrating an acoustic filter as an electrical equivalent circuit.

Assuming pressure ripple due to air that flows through the acoustic filter (that is, air that flows to exhaust path 42) as a voltage V and a flow rate of the air as a current I, the acoustic filter in the present embodiment can be represented as an R-C circuit in which through hole portion 44 forming a small pipe is denoted as a resistor R and air chamber 41 functioning as an air tank for storing air is denoted as a capacitor C, as shown in FIG. 4. Resistor R is in proportion to a length of through hole portion 44 formed to pass through partition wall portion 18, and a capacitance of capacitor C is in proportion to a volume of air chamber 41.

A voltage $V_0$ represents a voltage input to an electric circuit shown in FIG. 4, and it corresponds to pressure ripple when the acoustic filter is not provided. In addition, a voltage $V_1$ represents a voltage output from the electric circuit shown in FIG. 4, and it corresponds to pressure ripple when the acoustic filter is provided. Assuming that a frequency is denoted as f, a relational expression as below holds between voltage $V_0$ and voltage $V_1$:

$$\frac{V_1}{V_0} = \frac{1}{\sqrt{(\omega CR)^2 + 1}}$$

where ω represents an angular frequency, and a relational expression as below holds between frequency f and angular frequency ω.

$$\omega = 2\pi f$$

Therefore, a damping factor at the acoustic filter is expressed in the expression below as a function of frequency f.

$$\text{Damping factor} = -20\log_{10}\left(\frac{V_1}{V_0}\right)$$
$$= -20\log_{10}\frac{1}{\sqrt{(2\pi fCR)^2 + 1}}$$

Figure 5:
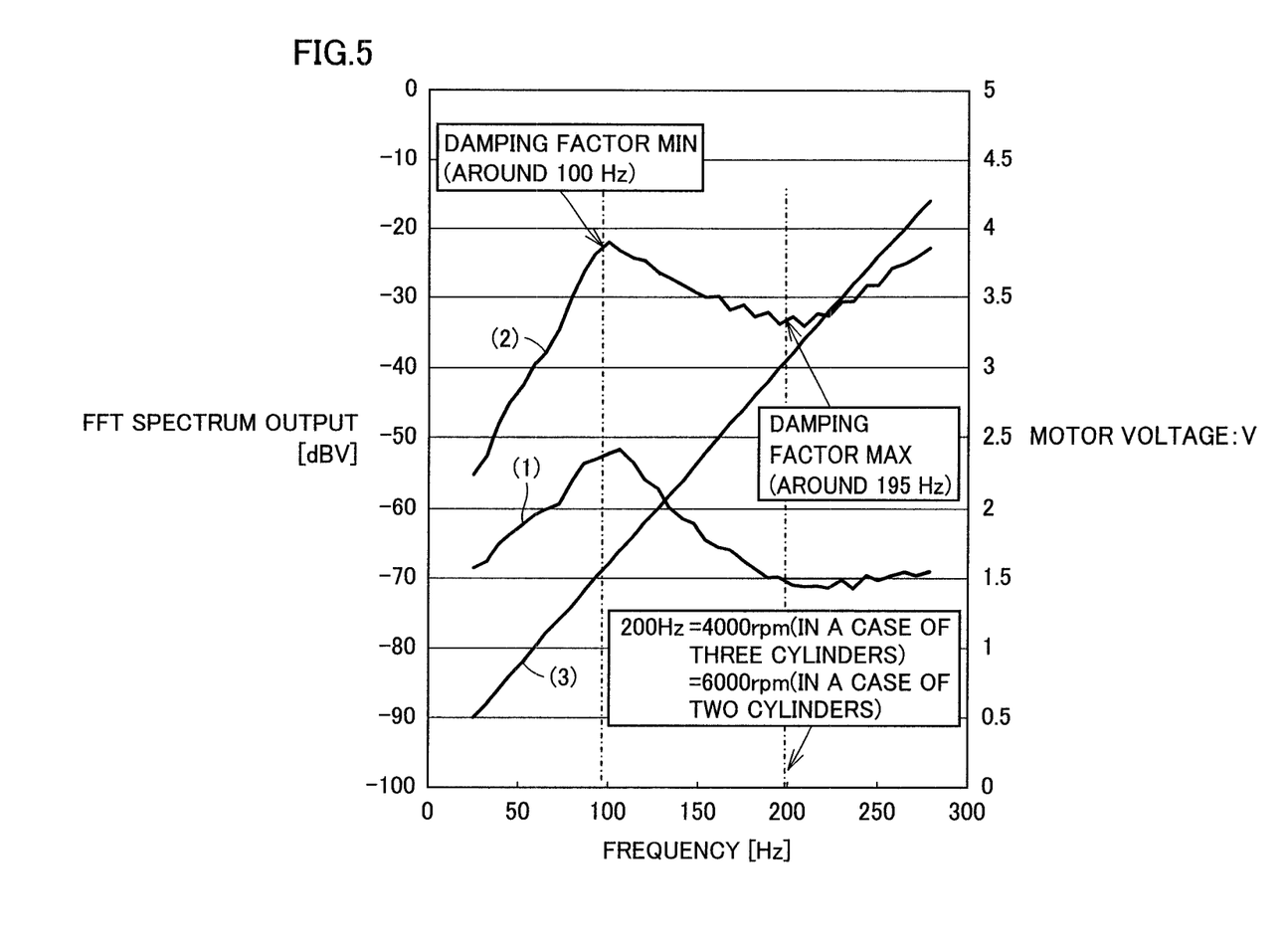
FIG. 5 is a graph showing relation between a frequency of the diaphragm pump and a reduction rate of pressure ripple.

The abscissa in FIG. 5 represents a frequency (unit: Hz), the left ordinate represents an output value (unit: dBV) from a spectrum analyzer using FFT (fast Fourier transform), and the right ordinate represents a voltage (unit: V) of motor 2 of diaphragm pump 1. Graph (1) shown in FIG. 5 shows relation between a frequency and an FFT spectrum output when the acoustic filter is provided. Graph (2) shows relation between a frequency and an FFT spectrum output when the acoustic filter is not provided. Graph (3) shows relation between a frequency and a motor voltage.

A difference in an FFT spectrum output value between graph (1) and graph (2) at a certain specific frequency indicates a damping factor of pressure ripple by the acoustic filter at that frequency. As shown in FIG. 5, the difference in the FFT spectrum output value between graph (1) and graph (2) is greater around a frequency of 195 Hz than around a frequency of 100 Hz. Namely, an effect of damping the pressure ripple achieved by the acoustic filter can more noticeably be obtained around the frequency of 195 Hz.

According to graph (3) in FIG. 5, the voltage of motor 2 around the frequency of 195 Hz attains to approximately 3V. In the case of three-cylinder diaphragm pump 1, a frequency when the speed of motor 2 is set to 4000 rpm is 200 Hz. Namely, in the case of diaphragm pump 1 in the present embodiment, when the voltage applied to motor 2 is set to approximately 3V and the speed of motor 2 is set to a little under 4000 rpm, an effect of reducing the pressure ripple through the acoustic filter (air chamber 41 and through hole portion 44) can more effectively be obtained.

As described above, diaphragm pump 1 in the present embodiment includes air chamber 41 in which a gas that has flowed out of pump chamber 12 flows, and partition wall portion 18 in which through hole portion 44 for restricting a flow rate of air that flows from air chamber 41 to exhaust port 43 is formed. Thus, as air chamber 41 and through hole portion 44 function as the acoustic filter, pressure ripple of a pressure of air exhausted from diaphragm pump 1 can be reduced.

The structure is such that air chambers 41 and through hole portions 44 corresponding to a plurality of pump chambers 12 respectively are provided independently and air chambers 41 and through hole portions 44 as many as pump chambers 12 are provided, however, the structure is not limited as such. For example, a structure may be such that a plurality of pump chambers 12 are provided, a single air chamber is provided, a single through hole portion serving as an exit of air from the air chamber is also formed, and gases that have flowed out of the plurality of pump chambers 12 gather in the single air chamber. According to such a structure as well, as compared with a parallel structure in which air chambers 41 and through hole portions 44 as many as the plurality of pump chambers 12 are provided, a damping factor equal from a viewpoint of an electrical equivalent circuit is obtained and an effect of damping pressure ripple is equal.

An overall configuration of a blood pressure monitor 300 for home use will now be described with reference to FIGS. 6 and 7. Referring to these figures, blood pressure monitor 300 includes a main body portion 301 containing a control device for blood pressure measurement, a cuff 302 attached to a blood pressure measurement site of the subject, for pressurizing the blood pressure measurement site with an air pressure, and an air tube 312 for coupling main body portion 301 and cuff 302 to each other.

Figure 6:
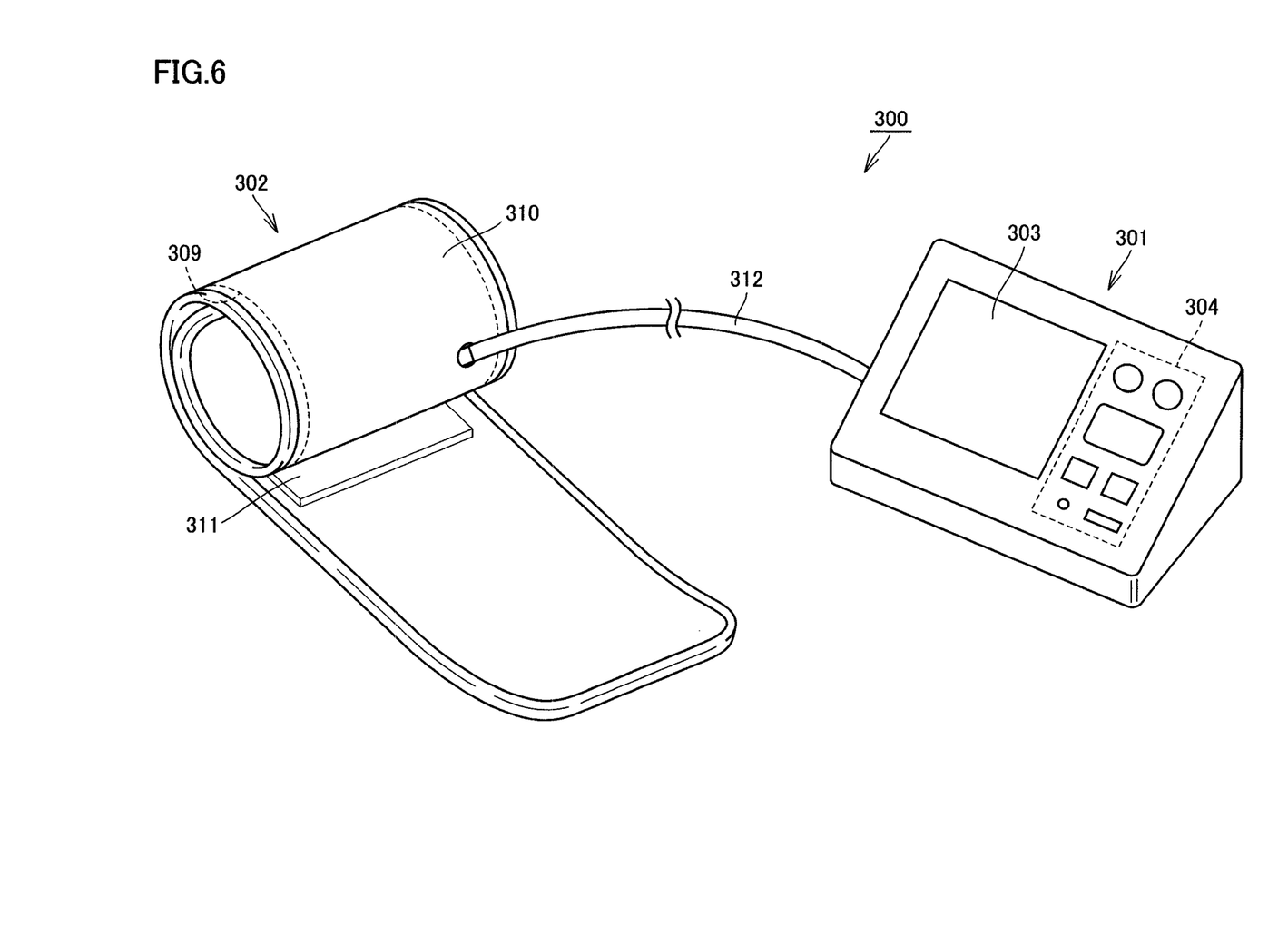
FIG. 6 is an overall perspective view showing appearance of a blood pressure monitor.

As shown in FIG. 6, main body portion 301 has on its outer surface, a display portion 303 provided such that the subject can recognize display contents such as a blood pressure value and an operation portion 304 provided such that the subject can externally operate blood pressure monitor 300. Cuff 302 has a bladder 309 for pressing, used for pressing an artery at the blood pressure measurement site (upper arm portion) of the subject, which is filled with air sent out from main body portion 301 and transferred through air tube 312 and stores the air. In addition, cuff 302 has a band 310 provided with bladder 309 on its inner surface side, for attachment to the upper arm portion of the subject and a hook and loop fastener 311 for winding band 310 around the upper arm portion and fixing the band thereto.

Figure 7:
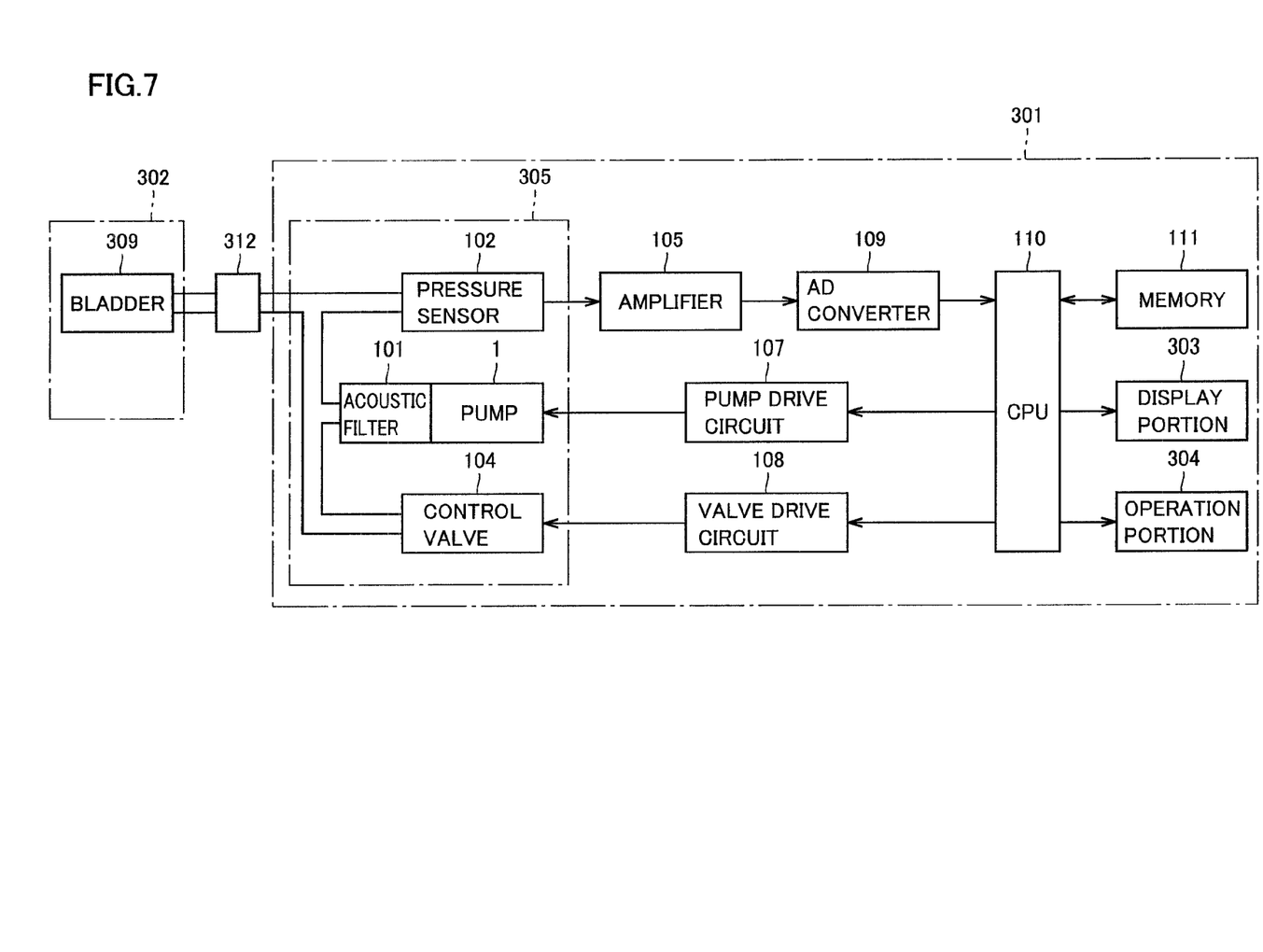
FIG. 7 is a block diagram showing an internal configuration of the blood pressure monitor.

As shown in FIG. 7, a blood pressure measurement air system 305 is provided in main body portion 301. Blood pressure measurement air system 305 includes a pressure sensor 102 serving as a pressure detection unit for detecting a pressure within cuff 302 (cuff pressure), diaphragm pump 1 for transferring a gas (air) to bladder 309 and raising the cuff pressure, and a control valve 104 for controlling a flow rate of the gas discharged from bladder 309.

Pressure sensor 102 outputs as a pulse wave signal, change in pulse pressure at the measurement site detected with bladder 309 contained in cuff 302 being interposed. Diaphragm pump 1 and control valve 104 adjust a level of pressurization by bladder 309 (air pressure). Bladder 309 is connected to pressure sensor 102, diaphragm pump 1 and control valve 104 through air tube 312.

In addition, a CPU (Central Processing Unit) 110 representing an exemplary measurement unit is provided in main body portion 301. CPU 110 controls such devices as pressure sensor 102, diaphragm pump 1 and control valve 104 and measures a blood pressure value, a pulse rate and the like of the subject based on a pressure value detected by pressure sensor 102.

Moreover, main body portion 301 includes an amplifier 105 for amplifying a signal indicating a cuff pressure output from pressure sensor 102, an A/D (analog/digital) converter 109 receiving an analog signal indicating the amplified cuff pressure output from amplifier 105, converting the analog signal to a digital signal, and outputting the digital signal to CPU 110, a pump drive circuit 107 for driving diaphragm pump 1, and a valve drive circuit 108 for adjusting opening and closing of control valve 104. Main body portion 301 includes a memory 111 for storing various programs and data for controlling measurement result data, a blood pressure measurement operation, a display operation by display portion 303, a communication operation, and the like.

When a blood pressure of the subject is measured with blood pressure monitor 300 configured as above, cuff 302 is attached to the blood pressure measurement site (upper arm) of the subject. Under the control by CPU 110, control valve 104 is closed so that air exhausted from diaphragm pump 1 flows out to bladder 309 in its entirety to pressurize bladder 309. On the other hand, control valve 104 is opened so that air in bladder 309 is emitted to the outside through control valve 104 to reduce the pressure in bladder 309. Here, CPU 110 converts a human body pressure pulse wave signal input to pressure sensor 102 to digital data and thereafter applies a prescribed algorithm to that data. Then, CPU 110 determines a systolic blood pressure and a diastolic blood pressure and calculates a pulse rate.

This blood pressure monitor 300 is structured such that air chamber 41 and through hole portion 44 implementing the acoustic filter are formed in diaphragm pump 1 and pressure ripple generated from diaphragm pump 1 can be eliminated. As pressure ripple of air exhausted from diaphragm pump 1 can be reduced, a sensed pressure pulse wave of a human body is not affected by noise and accuracy in blood pressure measurement can be improved. In addition, in the conventional diaphragm pump, pressurization noise was generated due to pressure ripple, however, the present structure can achieve reduction in pressurization noise of the pump itself owing to reduction in pump ripple.

In addition, it is not necessary to provide an acoustic filter for eliminating noise at an inlet of pressure sensor 102 provided to measure a human body pressure pulse wave. Therefore, as the number of parts for forming blood pressure monitor 300 can be reduced, cost for blood pressure monitor 300 can be reduced and a size of main body portion 301 of blood pressure monitor 300 can be made smaller.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A diaphragm pump for transporting a gas in accordance with change in volume of a pump chamber, comprising:
    an exhaust valve for permitting flow of the gas that flows out of the pump chamber and prohibiting flow thereof in a reverse direction; and
    a gas gathering body, the gas gathering body including an air chamber being formed therein in which the gas that has flowed out of the pump chamber through the exhaust valve flows, an exhaust port through which the gas is exhausted via an exhaust path to outside of the diaphragm pump, and a partition wall portion for partition between the air chamber and the exhaust path being formed by a part of the gas gathering body projecting inward,
    wherein in the partition wall portion, a through hole portion for communication between the air chamber and the exhaust path is formed,
    wherein the through hole portion restricts a flow rate of the gas that flows from the air chamber to the exhaust port, and
    wherein the through hole is formed in a central portion of the partition wall portion.

2. The diaphragm pump according to claim 1,
    wherein a plurality of the pump chambers are provided, and
    wherein a same number of the air chambers and a same number of the through hole portions as a number of the plurality of the pump chambers are provided.

3. The diaphragm pump according to claim 1,
    wherein a plurality of the pump chambers are provided,
    wherein a single said air chamber is provided, and
    wherein gases that have flowed out of the plurality of the pump chambers gather in the air chamber.

4. A blood pressure monitor, comprising:
    a cuff attached to a blood pressure measurement site of a subject and having a bladder filled with a gas;
    the diaphragm pump according to claim 1, for transferring the gas to said bladder;
    a pressure detection unit for detecting a pressure within said cuff; and
    a measurement unit for measuring a blood pressure of the subject based on a pressure value detected by said pressure detection unit.

* * * * *